United States Patent [19]
Schneider et al.

[11] Patent Number: 5,799,103
[45] Date of Patent: Aug. 25, 1998

[54] AUTOMATIC CHARACTERIZATION OF MECHANICAL AND/OR GEOMETRIC PROPERTIES OF STAPLE FIBER SAMPLES AND SUITABLE APPARATUS THEREFOR

[75] Inventors: August Schneider, Grossaitingen; Jochen Bader, Schwabmünchen; Franz Xaver Leimer, Wehringen, all of Germany

[73] Assignee: Hoechst Aktiengesellschaft, Germany

[21] Appl. No.: 355,855

[22] Filed: Dec. 15, 1994

[30] Foreign Application Priority Data

Dec. 17, 1993 [DE] Germany .................. 43 43 157.7

[51] Int. Cl.⁶ .................. G06K 9/00; G01L 5/04
[52] U.S. Cl. .................. 382/141; 382/152; 73/160; 356/429
[58] Field of Search .................. 382/100, 141, 382/152; 73/160; 356/429

[56] References Cited

U.S. PATENT DOCUMENTS

| | | | |
|---|---|---|---|
| 3,063,294 | 11/1962 | Oliver, Jr. | 73/160 |
| 3,899,927 | 8/1975 | Brassard et al. | 73/160 |
| 4,057,350 | 11/1977 | Craig | 356/199 |
| 4,270,252 | 6/1981 | Harrison | 202/250 |
| 4,274,746 | 6/1981 | Cardell et al. | 356/429 |
| 5,178,007 | 1/1993 | Ghorashi et al. | 73/159 |

FOREIGN PATENT DOCUMENTS

| | | | |
|---|---|---|---|
| 0 466 846 | 1/1991 | European Pat. Off. | G01N 21/89 |
| 14 73 750 | 4/1969 | Germany | D01H 13/32 |
| 1 648802 | 5/1971 | Germany | G01N 33/36 |
| 29 25 810 | 1/1980 | Germany | G01N 33/36 |
| 1183898 | 10/1985 | U.S.S.R. | G01N 33/36 |
| WO 92/02001 | 2/1992 | WIPO | G06K 9/00 |

OTHER PUBLICATIONS

Research Disclosure, Bd. 124, Aug. 1974 "Tow Crimp Analyser", pp. 13, 14.

*Primary Examiner*—Jose L. Couso
*Assistant Examiner*—Matthew C. Bella
*Attorney, Agent, or Firm*—Connolly & Hutz

[57] ABSTRACT

A method and apparatus for the automatic characterization of mechanical and/or geometric properties of stable fiber sample comprises presenting stable fiber samples in a magazine. The stable fiber samples are clamped in place for analysis by the apparatus which characterizes the mechanical and/or geometric properties of the fiber samples.

34 Claims, 2 Drawing Sheets

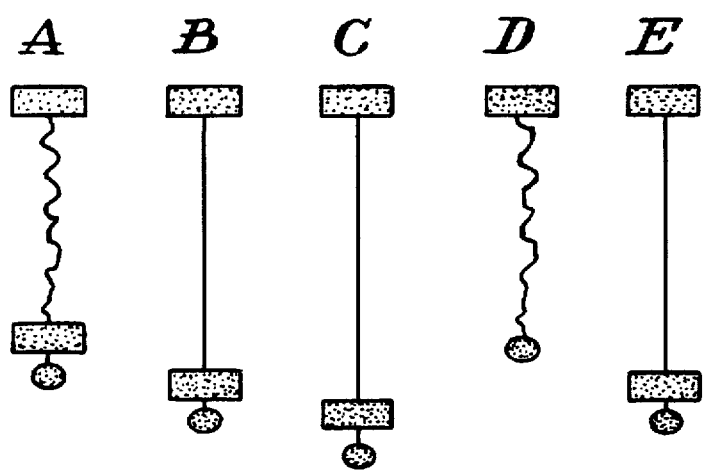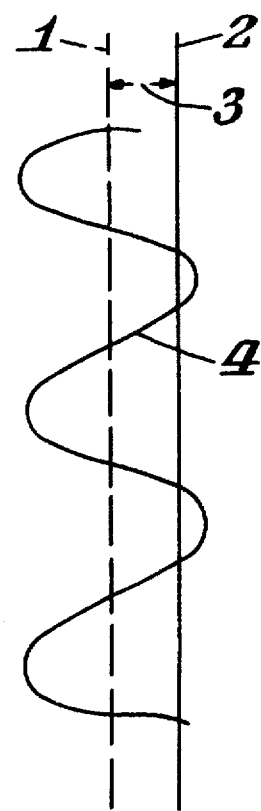

AUTOMATIC CHARACTERIZATION OF MECHANICAL AND/OR GEOMETRIC PROPERTIES OF STAPLE FIBER SAMPLES AND SUITABLE APPARATUS THEREFOR

BACKGROUND OF THE INVENTION

Automatic characterization of mechanical and/or geometric properties of staple fiber samples and suitable apparatus therefor The present invention relates to a method for the automatic characterization of mechanical and/or geometric properties of staple fiber samples, especially of crimp properties, such as the crimp contraction value or the number of crimp arcs of such fibers, and to an apparatus suitable for carrying out this method.

Methods for characterizing mechanical and/or geometrical properties of fibers, as for determining the crimp properties of fibers, are known per se.

One of the ways of characterizing the crimp properties of fibers is based on determining the crimp contraction. For this, the fiber is twice loaded with forces of a predetermined size, the first force being sufficiently small as not to cause crimp removal, and the second force being such that the crimp contraction is completely removed but the fiber is not stretched in the longitudinal direction. The difference in length between the crimp-contracted state and the extended state of the fiber in percent is known as the crimp contraction value. Measuring methods of this type are described for example in DE-A-2,925,810.

Such measurements are commonly carried out using the crimp balance. This is an apparatus in which a staple fiber to be characterized is clamped in at both ends, one of the clamps being attached to one end of the weighing beam. The other end of the weighing beam has an apparatus for receiving a mass. This mass creates the force which is necessary for removing the crimp from the in-test fiber in a defined manner.

The second clamp is movable in the fiber axis by means of a motor drive and sits on the shaft of a micrometer screw. The movable clamp is displaced to extend the fiber until the tensile force absorbed by the fiber equals the force created by the mass at the other end of the beam.

The balance is thus at equilibrium, which is detected photoelectrically and utilized, by means of an appropriate electronic system, to stop the clamp movement.

The change in length ΔL of the fiber corresponding to the distance the clamp has traveled can be read off on the micrometer screw. Optical measurements for determining the crimp properties have already been disclosed. For instance, SU-A-1,183,898 describes an optical determination of the stress-strain characteristics of crimped individual fibers. U.S. Pat. No. 4,057,350 discloses a method for determining the crimp of fiber tows by using the scattering of a laser beam as a measure of the degree of crimp. Further optical methods of measuring the crimp of running fiber tows are known from WO-A-92-2,001, U.S. Pat. No. 4,270,252 and RD-209,007. DE-C-1,473,750 describes the monitoring of the uniformity of the crimp of fiber tows by means of a mechanical method.

EP-B-466,846 discloses the use of image processing in the measurement of fiber parameters.

It is also known to characterize the crimp of fibers by determining the number of crimp arcs per unit length of the fiber at a predetermined fiber tension. This is usually done by means of the crimp balance and, furthermore, the number of crimp arcs of the clamped fibers is evaluated visually. The known method is not suitable for automation; moreover, it is personnel- and consequently cost-intensive.

DE-A-1,648,802 and U.S. Pat. No. 5,178,007 disclose apparatus for the automatic supply of samples to apparatus for characterizing fiber samples.

BRIEF DESCRIPTION OF THE DRAWINGS

Novel features and advantages of the present invention in addition to those mentioned above will become apparent to persons of ordinary skill in the art from a reading of the following detailed description in conjunction with the accompany drawings wherein:

FIG. 2 is a front elevational view of stable fiber samples during different measuring steps; and FIG. 3 is a diagrammatical view illustrating the mid-line of a stable fiber sample shifted by an offset from the longitudinal fiber axis.

DETAILED DESCRIPTION OF THE INVENTION

Figure 1:
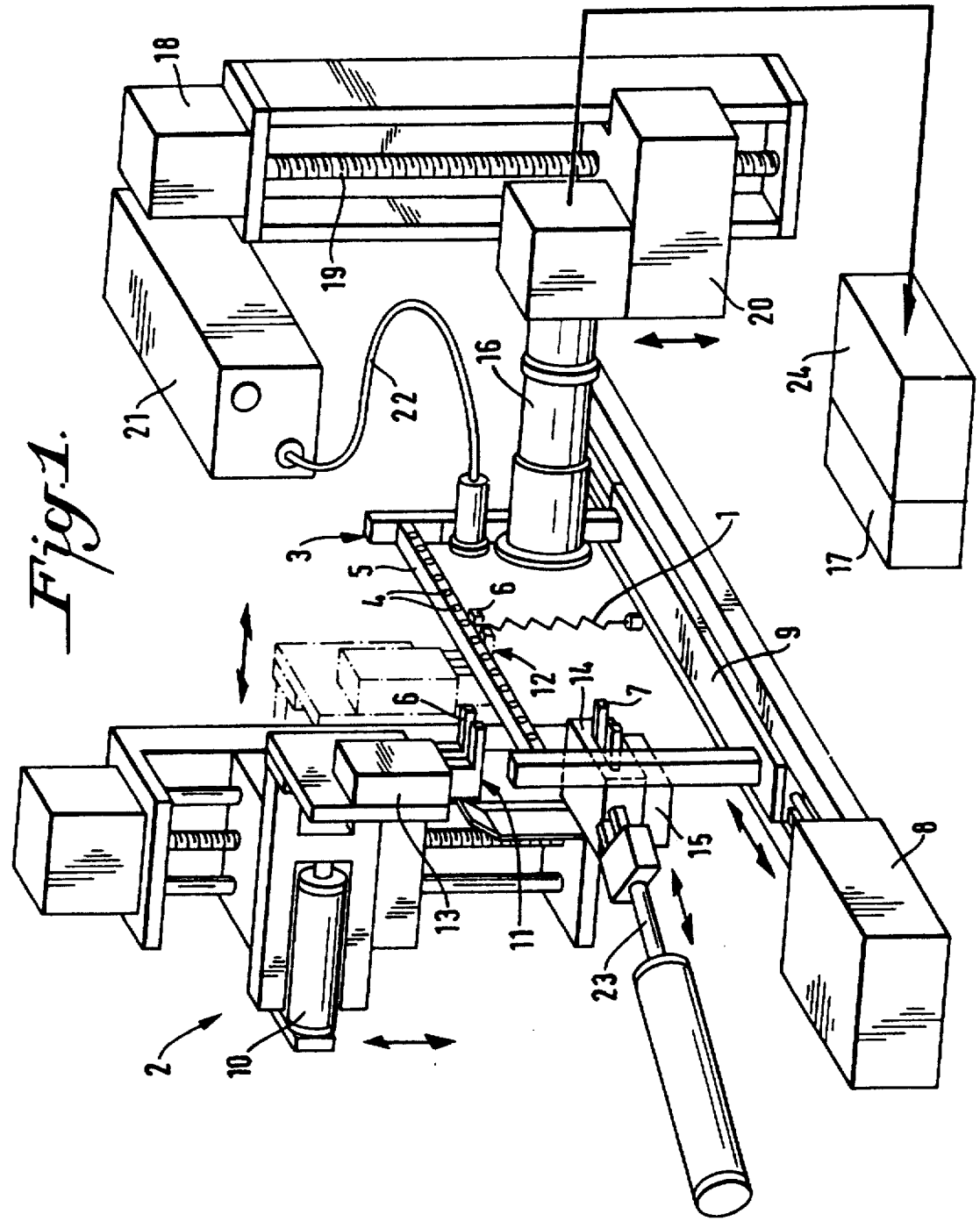
FIG. 1 is a perspective view of apparatus for the automatic characterization of mechanical and/or geometric properties of stable fiber samples.

There has now been found a method for characterizing mechanical and/or geometric properties of staple fibers, especially for characterizing the crimp of such fibers, which is simple and quick to carry out and which can be substantially automated.

The present invention accordingly provides a method for the automatic characterization of mechanical and/or geometric properties of staple fiber samples, comprising the following measures:

a) presenting staple fiber samples (1) in a magazine (3) which contains a plurality of clamps (4) for attaching in each case the upper end of a staple fiber sample (1), said clamps (4) being mounted on a clamp strip (5) and being movable by a predetermined distance on or with the clamp strip (5), b) connecting the filled magazine (3) to an apparatus (2) for characterizing mechanical and/or geometric properties of the staple fiber samples (1), said apparatus comprising at least one upper clamping jaw (6) and optionally a lower clamping jaw (7) for attaching the staple fiber sample (1) to be characterized, said upper clamping jaw (6) being movable and said magazine (3) being releasably connected to the apparatus (2) in such a way that the clamps (4) of the magazine (3) can be moved past in the vicinity of the upper clamping jaw (6) of the apparatus (2), c) moving the clamps (4), loaded with staple fiber samples (1) of the magazine (3) by a predetermined distance by means of a transporter (8), d) positioning a clamp (4) of the magazine (3) into the vicinity of the upper clamping jaw (6) of the apparatus (2) by means of an adjuster (9), e) moving the upper clamping jaw (6) of the apparatus (2) from a measuring position (11) into a transfer position (12) by means of a transporter (10), the upper clamping jaw (6) being present in the open position, f) closing the upper clamping jaw (6) of the apparatus (2) after attainment of the transfer position (12) by means of an opening and closing device (13) with transfer of the staple fiber sample (1) from clamp (4) of magazine (3), g) moving the upper clamping jaw (6) of the apparatus (2) together with the staple fiber sample (1) from the transfer position (12) into the measuring position (11) by means of the transporter (10), h) performing the characterization of the mechanical and/or geometric properties of the staple fiber samples (1) with the apparatus (2), and i) opening the upper clamping jaw (6) of the apparatus (2) after the characterization by means of the opening and closing device (13) and removing the staple fiber sample (1) from the apparatus (2).

The invention further provides an apparatus for automatic characterization of mechanical and/or geometric properties of staple fiber samples (1), comprising the following elements:

A) a magazine (3) for receiving staple fiber samples (1) which contains a plurality of clamps (4) for attaching in each case the upper end of a staple fiber sample (1), said clamps (4) being mounted on a clamp strip (5) and being movable by a predetermined length on or with the clamp strip (5), B) an apparatus (2) for characterizing mechanical and/or geometric properties of the staple fiber samples (1), said apparatus comprising at least one upper clamping jaw (6) and optionally a lower clamping jaw (7) for attaching the staple fiber sample (1) to be characterized, said upper clamping jaw (6) being movable and said magazine (3) being releasably connected to the apparatus (2) in such a way that the clamps (4) of the magazine (3) can be moved past in the vicinity of the upper clamping jaw (6) of the apparatus (2), C) a transporter (8) which makes it possible to move the clamps (4) of the magazine (3) by a predetermined distance, D) an adjuster (9) which makes it possible to position a clamp (4) of the magazine (3) in the vicinity of the upper clamping jaw (6) of the apparatus (2), E) a transporter (10) which makes it possible to move the upper clamping jaw (6) of the apparatus (2) out of a measuring position (11) into a transfer position (12) and back again, and F) an opening and closing device (13) which makes it possible to open and close the upper clamping jaw (6) of the apparatus (2) and to transfer the staple fiber sample (1) out of the magazine (3) and to remove the staple fiber sample (1) from the apparatus (2).

The method and apparatus of the present invention make it possible to characterize staple fibers of any kind. More particularly, the staple fibers can be uncrimped but are especially crimped.

The method and apparatus of the present invention make it possible in principle to carry out all measurements which can be used for characterizing mechanical and/or geometric properties of staple fiber samples.

Examples of the characterization of mechanical properties are recording of stress-strain diagrams, the measurement of the shrinkage, the shrinkage force, the crimp or a combination thereof.

In a particularly preferred embodiment of the present invention, the crimp properties of staple fibers are determined. The determination of the crimp properties can comprise for example the following measurements individually or in combination:

1. Determination of the number of crimp arcs per unit length of the fiber; this method will be described in detail later 2. Determination of the crimp contraction value $K_1$ according to the relation $$K_1 = (L_0 - L_1)/L_1$$

where $L_0$ is the defined clamped length of the crimped fiber and $L_1$ the length of the fiber on attainment of the decrimping force $F_{EK}$. $F_{EK}$ being the force which is required to decrimp the fiber in a first weighting. $F_{EK}$ can be determined in a separate measurement or simultaneously with the determination of $L_1$.

3. Determination of the residual crimp value $K_2$ according to the relation $$K_2 = (L_0 - L_2)/L_2$$

where $L_0$ is the defined clamped length of the crimped fiber and $L_2$ the length of the preweighted fiber on attainment of the decrimping force $F_{EK}$, and the preweighting of the fiber in the course of the determination of $K_2$ can take place after the determination of $K_1$ and comprises the following measures:

3.1 action on the fiber of a predetermined stability force $F_B$ over a predetermined period, for example $F_B=0.5$ cN/dtex, and 3.2 deweighting the fiber via the positioning of the lower clamping jaw (7) to a clamped length $<L_0$ and recovery phase of the fiber over a predetermined period through residence of the lower clamping jaw (7) in this position.

4. Determination of the crimp stability value KB by forming the ratio of $K_1$ and $K_2$, for example according to the relation $$KB = K_2/K_1$$

$K_1$ and $K_2$ can also be quoted in %.

A preferred example of the characterization of the geometric properties is the determination of the number of crimp arcs of staple fibers.

For the purposes of the present invention, a staple fiber sample comprehends not only bundles of staple fibers but also preferably individual staple fibers.

The method of the present invention is not restricted as regards the individual fiber linear density and the fiber-forming material.

Typical individual fiber linear densities range from 1 to 20 dtex.

Typical fiber-forming materials are polyphenylene sulfide, polyether ketone, glass or carbonized polyacrylonitrile (carbon fibers), polyacrylonitrile, polyamides, including the aramids, and polyester, in particular polyethylene terephthalate.

The invention will now be described by way of example with reference to the accompanying drawing.

The presentation of the staple fiber samples (1) to be characterized takes place in a magazine (3). This magazine contains a clamp strip (5) which carries the clamps (4). The charging of the clamps (4) can be manual or automatic.

For this, the upper ends of the staple fiber samples (1) are each attached to clamps (4). The lower ends of the staple fiber samples (1) can remain freely hanging in the magazine (3) or they are preferably weighted with a mass of predetermined size. This mass is usually transferred together with the staple fiber sample (1) into the apparatus (2).

The clamps (4) are mounted in the magazine (3) on the clamp strip (5) and are optionally releasably connected to this clamp strip (5). The clamps (4) are mounted on the clamp strip (5) to be movable or they can be moved together with it. The clamp strip (5) can be a rod horizontally mounted in the magazine (3). It can have devices to which the clamps (4) are in turn releasably connected, for example by clamping. Preferably the clamps (4) remain in the magazine (3) following the transfer of the staple fiber sample (1) into the apparatus (2).

After the charging of the magazine (3) with staple fiber samples (1), it is manually or automatically connected to the apparatus (2) for characterizing mechanical and/or geometric properties of staple fiber samples (1). This can be via any desired mechanical connection which makes it possible to fix the position of the magazine (3) in relation to the apparatus (2).

The term "connecting the filled magazine (3) to the apparatus (2)" also comprehends an embodiment where merely the clamp strip (5) is removed for the purpose of charging with the staple fibre samples (1) and then fixed back in the magazine (3).

Apparatus (2) comprises at least one upper clamping jaw (6) for attaching the staple fiber sample (1) to be characterized. If desired, a lower clamping jaw (7) may be provided as well. For characterization, the staple fiber sample (1) is clamped into the upper clamping jaw (6) or into the upper clamping jaw (6) and the lower clamping jaw (7).

For the purpose of transferring a staple fiber sample (1) from the magazine (3), a clamp (4), loaded with a staple fiber sample (1), of the magazine (3) is moved by a predetermined distance by means of a transporter (8) and positioned by means of an adjuster (9) into the vicinity, preferably above the upper clamping jaw (6) of the apparatus (2). Instead of the clamp (4) it is also possible to move the apparatus (2).

Then the upper clamping jaw (6) of the apparatus (2) is moved out of a measuring position (11) into a transfer position (12) by means of a transporter (10). For this the upper clamping jaw (6) is present in the open position.

This movement of the upper clamping jaw (6) is preferably in the horizontal direction and at right angles to the direction of movement of the clamps (4) of the magazine (3).

On attainment of a transfer position (12) the upper clamping jaw (6) of the apparatus (2) is closed and grips the staple fiber sample (1). This is effected by means of an opening and closing device (13).

To transfer the staple fiber sample (1) into the apparatus (2), the closed upper clamping jaw (6) is moved together with the staple fiber sample (1) and optionally with the clamp (4) from the transfer position (12) into the measuring position (11). This is effected by means of the transporter (10). The movement of the upper clamping jaw (6) and the staple fiber sample (1) clamped therein effects a transfer of the staple fiber sample (1) into the apparatus (2).

On attainment of the measuring position, the characterization of the mechanical and/or geometric properties of the staple fiber sample (1) can be carried out with the apparatus (2).

Depending on the desired method of measurement, the staple fiber sample (1) can be characterized immediately after transfer, or first a further positioning or fixing of the staple fiber sample (1) for example by clamping the lower portion of the staple fiber sample (1) in a lower clamping jaw (7) of the apparatus (2), is effected by means of an opening and closing device (14).

Following characterization of the staple fiber sample (1) in the apparatus (2), the upper clamping jaw (6) and, if present, the lower clamping jaw (7) is opened by means of the opening and closing devices (13) and (14) and the staple fiber sample (1) is removed from the apparatus (2).

In a preferred embodiment of the invention, the crimp contraction value of the staple fiber sample (1) is determined, the necessary measurement of the pretension being carried out by means of a force sensor (15) (not depicted) which is subject to the action of the upper clamping jaw (6) or the lower clamping jaw (7).

The preferred embodiment as per the drawing depicts automatic determination of the number of crimp arcs per unit length of crimped staple fibers.

In said preferred embodiment, the number of crimp arcs per unit length of the staple fiber sample (1) is determined with the apparatus (2) as follows:

h3) creating an image of predetermined length and predetermined width of the staple fiber sample (1) by means of an imager (16) which is preferably movable in the direction of the longitudinal fiber axis, h4) creating from the image a digital grid whose pixels are deposited in the form of numerical values in a memory (17), said numerical values representing measurements of the lightness at the respective locus of the image, and h5) determining from the digital grid the number of crimp arcs in the depicted staple fiber sample by means of digital image processing.

In the depicted preferred embodiment, the apparatus comprises an imager (16) which serves to create an image of predetermined length and predetermined width of the staple fiber sample (1) present in the apparatus (2) and which is movable in the direction of the longitudinal fiber axis, said imager (16) driving a data processor (24) which creates from the image a digital grid whose pixels are deposited in the form of numerical values in the memory (17). Instead of an imager (16), which is movable in the direction of the longitudinal fiber axis an image may be created by an imager (16) in a fixed position and a digital grid may be formed from this image as described above and whose pixels are deposited in the memory (17) and are processed in the manner described above.

Image processing for the purposes of the present invention is the analysis of images or the reconstruction of objects from their image. Image processing serves the purpose of pattern recognition. Pattern recognition is used for the extraction of features and for classification.

In a particularly preferred embodiment of the method of the present invention, the digital image processing in step h5) is carried out as follows:

h6) creating in the image a longitudinal fiber axis which corresponds to the course which the staple fiber sample (1) would have in the extended state, h7) creating in the image a mid-line which extends within the longitudinal fiber axis of step h6) or parallel thereto at a predetermined distance and which intersects the staple fiber sample (1) image created in step h3) at least repeatedly, and h8) determining the number of intersections between the mid-line created in step h7) and the staple fiber sample (1) image created in step h3) as a measure of the number of crimp arcs in the staple fiber sample (1) appearing in the image.

The longitudinal fiber axis can be defined for example by a compensating curve or by segmentally defined compensating curves. The data for calculating the compensating curve are deposited via the imager (16) and the data processor (24) in the memory (17). The compensating curve is calculated in the data processor (24).

The mid-line in step h7) can extend in the longitudinal fiber axis of step h6) or be created by an offset from one of the parameters of the compensating curve.

The determination of the number of intersections in step h8) can be determined by determining the zero value of the difference curve formed mid-line and image of the staple fiber sample (crimp curve) (connection between the digitalized fiber coordinates from point to point).

The imager (16) can be any desired camera capable of converting an image into electronic signals, for example a video camera.

The invention further provides the use of an imager for the determination of the number of crimp arcs per unit length of a fiber sample, which fiber sample is clamped at least at one end and which fiber sample is preferably under a predetermined prestress and is free hanging.

Preference is given to a line camera, since it ensures an adequate resolution of the fiber image to be examined and makes it possible to differentiate even small and very small production-induced crimp arcs.

In a particularly preferred embodiment, the line camera depicts 2048 pixels in each case transversely to the staple fiber sample (1). This makes a resolution of 0.01 mm possible, which allows a depiction of all customary occurring crimp arcs.

The movement of the imager (16) in the direction of the longitudinal fiber axis is preferably effected by means of a step motor (18).

In the depicted preferred variant, the step motor (18) acts via a spindle (19) on a fastening device (20) which is attached to the apparatus (2) and to which the imager (16) is attached.

In the depicted preferred variant, in the creation of the image, the imager (16) is illuminated by a light source (21) so that the staple fiber sample (1) is situated at the intersection between the light source (21) and the imager (16).

Particular preference is given to using a light source (21) which is a mirror (not depicted) which is irradiated by an optical waveguide (22) and which illuminates the imager (16) indirectly. This embodiment ensures a particularly low thermal stress on the staple fiber sample (1).

Particular preference for the illumination is given to a cold light lamp which illuminates the imager (16) indirectly via a mirror. This embodiment is associated with a particularly favorable thermal stress on the staple fiber sample (1).

The magazine (3) can contain the staple fiber samples (1) in any desired arrangement, preferably in a linear arrangement or in a circular arrangement.

In the depicted preferred variant, the staple fiber sample (1) is after the characterization of the mechanical and/or geometric properties removed from the apparatus (2) by an arm (23). The use of a pneumatically or hydraulically operated arm (23) is particularly preferred since no air draft is desirable in the removal of the staple fiber sample.

After the measurement step 2 (determination of $L_1$), the fiber is loaded by the force $F_B$. The force $F_B$ is a fixed value, for example 0.5 cN/dtex referring to the denier of the fiber. After loading of the fiber with the fixed force $F_B$, the fiber is relieved so that the fiber relaxes for a period of time. Then, after a defined time period, the measurement of $K_2$ follows as set out above in connection with the measurement of $K_1$.

For clarity, FIG. 2 illustrates the different measurement steps. The measurement steps are as follows:

A Starting point of the measurement; Determination of the number of crimps;

B Determination of $K_1$; Elongation and measurement of $F_{EK}$; Distance of clamping jaws=$L_1$;

C Determination of $K_2$; load with predetermined force, for example for 1 minute;

D Determination of $K_2$; relaxation of the fiber, for example, for 1 minute; and E Determination of $K_2$; elongation and measurement of $F_{EK}$; Distance of clamping jaws=$L_2$.

The mid-line can be shifted by an offset from the longitudinal fiber axis. This is illustrated in FIG. 3 of the drawings. FIG. 3 makes it clear that the mid-line is shifted by an offset from the longitudinal fiber axis. The following reference characters are used in the drawing:

1 Longitudinal fiber axis (step h6),

2 Mid-line (step h7),

3 Offset, and

4 Crimped fiber.

The longitudinal fiber axis of step h7 can be defined by segmentally defined compensating curves. For example, each of these compensating curves needs about four parameters which define one curve. Such curve is a mathematical formula which is called a spline function. According to one preferred embodiment of the present invention, the mid-line is moved (shifted) by a fixed value from the position of the longitudinal fiber axis. Such a mid-line can be obtained by addition of a fixed value to one of the parameters of the spline functions of the curve of the longitudinal fiber axis. Finally, this leads to a new set of segmentally defined curves defining the shifted mid-line. Again, these steps and techniques are well know by persons skilled in the art.

The number of intersections between the shifted mid-line 2 of FIG. 3 can be obtained by observing the course of mid-line 2 of FIG. 3 can be obtained by observing the course of mid-line 2 and the course of the fiber curve. The intersections can be detected and counted, for example, by known computer programs.

What is claimed is:

1. A method for the automatic characterization of mechanical and/or geometric properties of staple fiber samples, comprising the following measures:

a) presenting staple fiber samples (1) in a magazine (3) which contains a plurality of clamps (4) for attaching in each case the upper end of a staple fiber sample (1), said clamps (4) being mounted on a clamp strip (5) and being movable by a predetermined distance with the clamp strip (5), b) connecting the filled magazine (3) to an apparatus (2) for characterizing mechanical and/or geometric properties of the staple fiber samples (1), said apparatus comprising at least one upper clamping jaw (6) and optionally a lower clamping jaw (7) for attaching the staple fiber sample (1) to be characterized, said upper clamping jaw (6) being movable and said magazine (3) being releasably connected to the apparatus (2) in such a way that the clamps (4) of the magazine (3) can be moved past in the vicinity of the upper clamping jaw (6) of the apparatus (2), c) moving the clamps (4), loaded with staple fiber samples (1) of the magazine (3) by a predetermined distance by means of a transporter (8), d) positioning a clamp (4) of the magazine (3) into the vicinity of the upper clamping jaw (6) of the apparatus (2) by means of an adjuster (9), e) moving the upper clamping jaw (6) of the apparatus (2) from a measuring position (11) into a transfer position (12) by means of a transporter (10), the upper clamping jaw (6) being present in the open position, f) closing the upper clamping jaw (6) of the apparatus (2) after attainment of the transfer position (12) by means of an opening and closing device (13) with transfer of the staple fiber sample (1) from the clamp (4) of magazine (3), g) moving the upper clamping jaw (6) of the apparatus (2) together with the staple fiber sample (1) from the transfer position (12) into the measuring position (11) by means of the transporter (10), h) performing the characterization of the mechanical and/or geometric properties of the staple fiber samples (1) with the apparatus (2), and i) opening the upper clamping jaw (6) of the apparatus (2) after the characterization by means of the opening and closing device (13) and removing the staple fiber sample (1) from the apparatus (2).

2. The method of claim 1, wherein in the course of the presentation of staple fiber samples (1) in step a) these are each weighted at their lower end with a mass of predetermined size.

3. The method of claim 1 for the automatic determination of the crimp contraction value of crimped staple fibers, comprising the following measures:

a1) presenting crimped staple fiber samples (1) in step a), d1) presetting the upper clamping jaw (6) and the lower clamping jaw (7) in the open position in step d), g1) closing the lower clamping jaw (7) of the apparatus (2) after the movement of the upper clamping jaw (6) into the measuring position (11) (step g) by means of an opening and closing device (14) while clamping the lower end of the staple fiber sample (1) into the lower clamping jaw (7), h1) determining the crimp contraction value of the staple fiber sample (1) with the apparatus (2) in step h) in a manner known per se, and i1) opening the upper and lower clamping jaws (6, 7) of the apparatus (2) after the characterization by means of the opening and closing devices (13, 14) and removing the staple fiber sample (1) from the apparatus (2) in step i).

4. The method of claim 3, wherein the crimp contraction value $K_1$ is determined according to the relation $$K_1=(L_0-L_1)/L_1$$

where $L_0$ is the defined clamped length of the crimped fiber and $L_1$ the length of the fiber on attainment of the decrimping force $F_{EK}$, $F_{EK}$ being the force which is required to decrimp the fiber in a first weighting.

5. The method of claim 3, wherein the residual crimp value $K_2$ is determined according to the relation $$K_2=(L_0-L_2)/L_2$$

where $L_0$ is the defined clamped length of the crimped fiber and $L_2$ the length of the preweighted fiber on attainment of the decrimping force $F_{EK}$, and the preweighting of the fiber in the course of the determination of $K_2$ comprises the following measures:

action on the fiber of a predetermined stability force $F_B$ over a predetermined period, and deweighting the fiber via the positioning of the lower clamping jaw (7) to a clamped length $<L_0$ and recovery phase of the fiber over a predetermined period through residence of the lower clamping jaw (7) in this position.

6. The method of claim 3, wherein the crimp stability $K_B$ is determined according to the relation $$KB=K_2/K_1$$

where $K_1=(L_0-L_1)/L_1$ and $K_2=(L_0-L_2)/L_2$ where $L_0$ is the defined clamped length of the crimped fiber and $L_1$ the length of the fiber on attainment of the decrimping force $F_{EK}$, $F_{EK}$ being the force which is required to decrimp the fiber in a first weighting and $L_2$ the length of the preweighted fiber on attainment of the decrimping force.

7. The method of claim 3, wherein the necessary fiber tension measurement in the course of the determination of the crimp contraction value of the staple fiber sample (1) is effected by means of a force sensor (15) which is subject to the action of the upper clamping jaw (6) or the lower clamping jaw (7).

8. The method of claim 1 for the automatic determination of the number of crimp arcs per unit length of crimped staple fibers, comprising the following measures:

a1) presentation in step a) of crimped staple fiber samples (1), and h2) in step h) using the apparatus (2) to determine the number of crimp arcs per unit length of the staple fiber sample (1) in the following manner:

h3) creating an image of predetermined length and predetermined width of the staple fiber sample (1) by means of an imager (16) which is preferably movable in the direction of the longitudinal fiber axis, h4) creating from the image a digital grid whose pixels are deposited in the form of numerical values in a memory (17), said numerical values representing measurements of the lightness at the respective locus of the image, and h5) determining from the digital grid the number of crimp arcs in the depicted staple fiber sample by means of digital image processing.

9. The method of claim 8, wherein in the course of the presentation of staple fiber samples (1) in step a) these are each weighted at their lower end with a mass of predetermined size and the so weighted staple fiber samples (1) are transferred into the apparatus (2).

10. The method of claim 8 for the automatic determination of the number of crimp arcs per unit length of crimped staple fibers, comprising the following measures:

d1) presetting the upper clamping jaw (6) and the lower clamping jaw (7) in the open position in step d), g1) closing the lower clamping jaw (7) of the apparatus (2) after the movement of the upper clamping jaw (6) into the measuring position (11) (step g) by means of an opening and closing device (14) while clamping the lower end of the staple fiber sample (1) with the lower clamping jaw (7), and i1) opening the upper and lower clamping jaws (6, 7) of the apparatus (2) after the characterization by means of the opening and closing devices (13, 14) and removing the staple fiber sample (1) with the clamp (4) from the apparatus (2) in step i).

11. The method of claim 8, wherein not only the number of crimp arcs per unit length of the staple fiber sample (1) is determined but also the tension on the staple fiber sample (1) at the creation of the image, the determination of the fiber tension being effected by means of a force sensor (15) which is subject to the action of the upper clamping jaw (6) or the lower clamping jaw (7).

12. The method of claim 8, wherein the digital image processing of step h5) is carried out as follows:

h6) creating in the image a longitudinal fiber axis which corresponds to the course which the staple fiber sample (1) would have in the extended state, h7) creating in the image a mid-line which extends within the longitudinal fiber axis of step h6) or parallel thereto at a predetermined distance and which intersects the staple fiber sample (1) image created in step h3) at least repeatedly, and h8) determining the number of intersections between the mid-line created in step h7) and the staple fiber sample (1) image created in step h3) as a measure of the number of crimp arcs in the staple fiber sample (1) appearing in the image.

13. The method of claim 8, wherein the imager (16) is a line camera.

14. The method of claim 8, wherein the movement of the imager (16) in the direction of the longitudinal fiber axis is effected by means of a step motor (18).

15. The method of claim 14, wherein the step motor (18) acts via a spindle (19) on a fastening device (20), mounted on apparatus (2), to which the imager (16) is attached.

16. The method of claim 8, wherein, in the creation of the image, the imager (16) is illuminated by a light source (21) so that the staple fiber sample (1) is situated between the light source (21) and the imager (16).

17. The method of claim 16, wherein the light source (21) is a mirror which is irradiated by an optical waveguide (22) and illuminates the imager (16) indirectly.

18. The method of claim 8, wherein the illumination is effected using a cold light lamp which illuminates the imager (16) indirectly via a mirror.

19. The method of claim 1, wherein the magazine (3) contains the staple fiber samples (1) in a linear arrangement.

20. The method of claim 1, wherein the magazine (3) contains the staple fiber samples (1) in a circular arrangement.

21. The method of claim 1, wherein the staple fiber sample (1) is after the characterization of the mechanical and/or geometric properties removed from the apparatus (2) by a pneumatically or hydraulically operated arm (23).

22. Apparatus for automatic characterization of mechanical and/or geometric properties of staple fiber samples (1), comprising the following elements:

A) a magazine (3) for receiving staple fiber samples (1) which contains a plurality of clamps (4) for attaching in each case the upper end of a staple fiber sample (1), said clamps (4) being mounted on a clamp strip (5) and being movable by a predetermined length with the clamp strip (5), B) an apparatus (2) for characterizing mechanical and/or geometric properties of the staple fiber samples (1), said apparatus comprising at least one upper clamping jaw (6) and optionally a lower clamping jaw (7) for attaching the staple fiber sample (1) to be characterized, said upper clamping jaw (6) being movable and said magazine (3) being releasably connected to the apparatus (2) in such a way that the clamps (4) of the magazine (3) can be moved past in the vicinity of the upper clamping jaw (6) of the apparatus (2), C) a transporter (8) which makes it possible to move the clamps (4) of the magazine (3) by a predetermined distance, D) an adjuster (9) which makes it possible to position a clamp (4) of the magazine (3) in the vicinity of the upper clamping jaw (6) of the apparatus (2), E) a transporter (10) which makes it possible to move the upper clamping jaw (6) of the apparatus (2) out of a measuring position (11) into a transfer position (12) and back again, and F) an opening and closing device (13) which makes it possible to open and close the upper clamping jaw (6) of the apparatus (2) and to transfer the staple fiber sample (1) out of the magazine (3) and to remove the staple fiber sample (1) from the apparatus (2).

23. The apparatus of claim 22, wherein apparatus (2) comprises for determining the fiber tension of a force sensor (15) which is subject to the action of the upper clamping jaw (6) or the lower clamping jaw (7).

24. The apparatus of claim 22, comprising an imager (16) which serves to create an image of predetermined length and predetermined width of the staple fiber sample (1) present in the apparatus (2) and which is preferably movable in the direction of the longitudinal fiber axis, said imager (16) driving a data processor (24) which creates from the image a digital grid whose pixels are deposited in the form of numerical values in a memory (17), the numerical values representing measurements of the lightness at the respective locus of the image.

25. The apparatus of claim 24, wherein the data processor (24) makes it possible to determine the number of crimp arcs in the depicted staple fiber sample from the digital grid by means of digital image processing.

26. The apparatus of claim 24, wherein the imager (16) is a line camera.

27. The apparatus of claim 24, wherein the movement of the imager (16) in the direction of the longitudinal fiber axis is effected by means of a step motor (18).

28. The apparatus of claim 27, wherein the step motor (18) acts via a spindle (19) on a fastening device (20), mounted on apparatus (2), to which the imager (16) is attached.

29. The apparatus of claim 24, wherein, in the creation of the image, the imager (16) is illuminated by a light source (21) so that the staple fiber sample (1) is situated at the intersection between the light source (21) and the imager (16).

30. The apparatus of claim 29, wherein the light source (21) is a mirror which is irradiated by an optical waveguide (22) and illuminates the imager (16) indirectly.

31. The apparatus of claim 24, wherein the illumination is effected using a cold light lamp which illuminates the imager (16) indirectly via a mirror.

32. The apparatus of claim 22, wherein the magazine (3) contains the staple fiber samples (1) in a linear arrangement.

33. The apparatus of claim 22, wherein the magazine (3) contains the staple fiber samples (1) in a circular arrangement.

34. The apparatus of claim 22, wherein the staple fiber sample (1) is after the characterization of the mechanical and/or geometric properties removed from the apparatus (2) by a pneumatically or hydraulically operated arm (23).

* * * * *

UNITED STATES PATENT AND TRADEMARK OFFICE
CERTIFICATE OF CORRECTION

PATENT NO.  : 5,799,103
DATED       : August 25, 1998
INVENTOR(S) : August Schneider, et al.

It is certified that error appears in the above-identified patent and that said Letters Patent is hereby corrected as shown below:

Column 8, lines 26 and 27, delete redundant clause "of mid-line 2 of FIG 3. can be obtained by observing the course".

Signed and Sealed this

Twenty-ninth Day of December, 1998

Attest:

BRUCE LEHMAN

Attesting Officer

Commissioner of Patents and Trademarks